US012605179B2

(12) United States Patent
Wan et al.

(10) Patent No.: US 12,605,179 B2
(45) Date of Patent: Apr. 21, 2026

(54) ULTRASONIC SURGICAL INSTRUMENTS WITH TRANSLATIONAL CAPABILITY

(71) Applicant: Genesis Medtech (USA) Inc., Saint Louis Park, MN (US)

(72) Inventors: Shan Wan, Plymouth, MN (US); Brendan Reimer, Eden Prairie, MN (US)

(73) Assignee: Genesis Medtech (USA) Inc., Saint Louis Park, MN (US)

( * ) Notice: Subject to any disclaimer, the term of this patent is extended or adjusted under 35 U.S.C. 154(b) by 229 days.

(21) Appl. No.: 18/197,716

(22) Filed: May 15, 2023

(65) Prior Publication Data

US 2024/0382225 A1 Nov. 21, 2024

Related U.S. Application Data

(60) Provisional application No. 63/341,861, filed on May 13, 2022.

(51) Int. Cl.
| | |
|---|---|
| *A61B 17/32* | (2006.01) |
| *B06B 1/06* | (2006.01) |
| *B06B 3/00* | (2006.01) |

(52) U.S. Cl.
CPC .... *A61B 17/320068* (2013.01); *B06B 1/0611* (2013.01); *B06B 3/00* (2013.01); *A61B 2017/320082* (2017.08); *B06B 2201/76* (2013.01)

(58) Field of Classification Search
CPC ........... A61B 17/320068; A61B 2017/320082; B06B 3/00
See application file for complete search history.

(56) References Cited

U.S. PATENT DOCUMENTS

2010/0331869 A1* 12/2010 Voegele ............... H10N 30/503
606/169

* cited by examiner

*Primary Examiner* — Ashley L Fishback
(74) *Attorney, Agent, or Firm* — Porter Wright Morris & Arthur LLP

(57) ABSTRACT

An ultrasonic surgical instrument having an ultrasonic resonant frequency when operatively connected to an ultrasonic generator, the surgical instrument including an ultrasonic transducer assembly adapted for converting electrical energy into longitudinal vibrational motion at an ultrasonic frequency, the transducer assembly having an axial passageway extending proximally from a distal end of the transducer through at least a portion of a length of the transducer assembly, an ultrasonic waveguide having a proximal portion and a distal end, and an end effector at the distal end of the waveguide. The proximal portion of the waveguide is adapted to be operatively and selectively coupled within the axial passageway of the ultrasonic transducer such that the waveguide will transmit ultrasonic energy from the transducer to the end effector, and further wherein the waveguide is selectively coupleable within the transducer to provide at least two different effective lengths without altering the resonant frequency of the instrument.

20 Claims, 6 Drawing Sheets

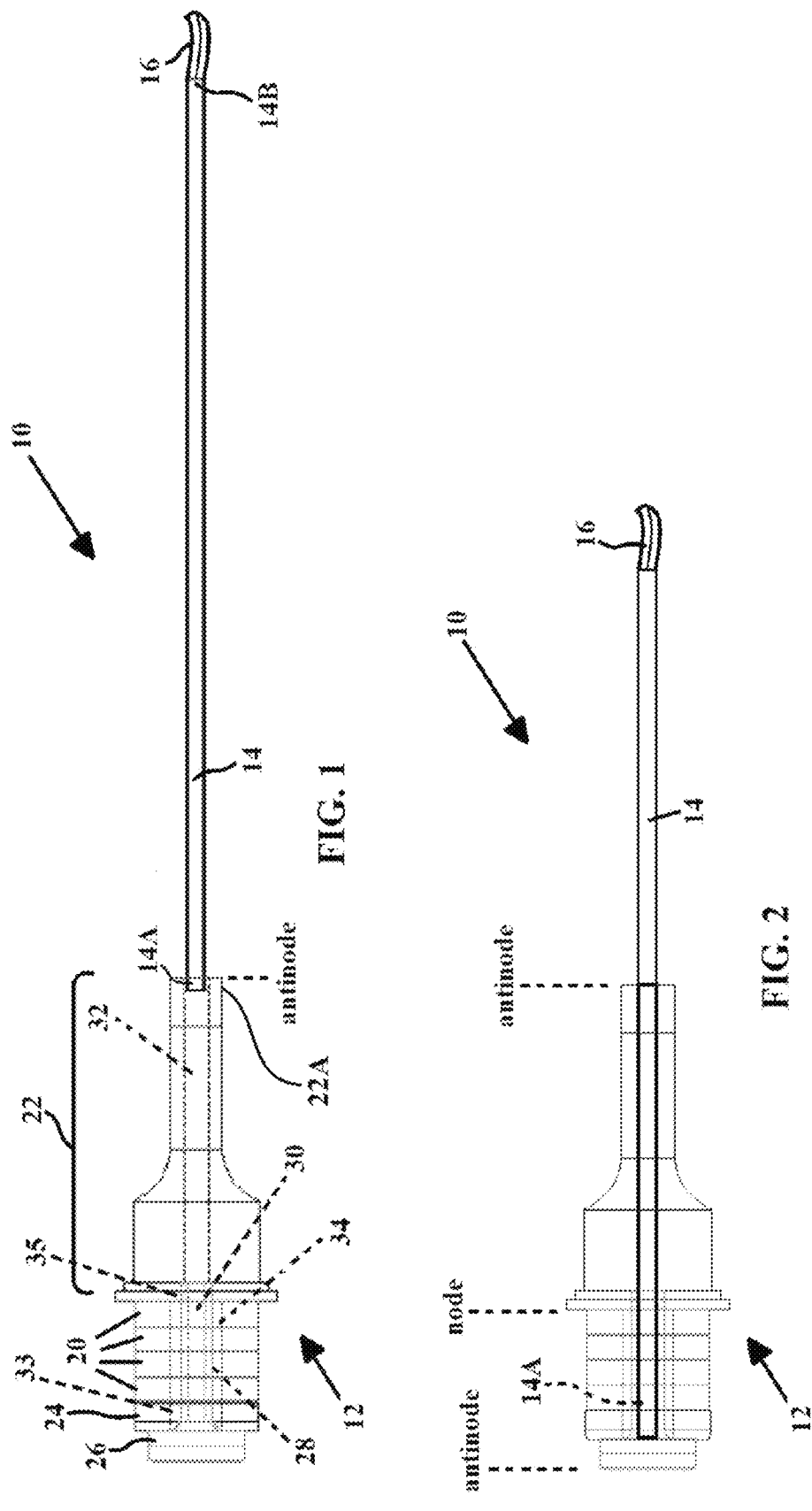

ULTRASONIC SURGICAL INSTRUMENTS WITH TRANSLATIONAL CAPABILITY

CROSS REFERENCE TO RELATED APPLICATIONS

This application claims priority to U.S. Provisional Patent Application No. 63/341,861, filed on May 13, 2022, entitled "ULTRASONIC SURGICAL INSTRUMENTS WITH TRANSLATIONAL CAPABILITY." The entire disclosure of the foregoing provisional patent application is incorporated by reference herein.

BACKGROUND

Mechanical tools have been used in a variety of open surgical procedures for centuries. They became the natural extension of surgeons' hands to perform various specific surgical functions such as treating diseased tissue and organs or repairing internal structures. Since the 1980s, laparoscopic and endoscopic procedures have emerged as minimal invasive solution for a wide spectrum of surgical procedures such as cholecystectomies, appendectomies, hernia repair, and other more complex procedures. Extensive improvements in traditional tools have been made to support surgical cutting, dissection, coagulation, tissue manipulation and tissue management. Energy driven devices such as advanced RF bipolar and ultrasonic instruments such as scalpel systems have been gaining popularity due to this transition, as well as the continued emergence of robotic-assisted surgery.

For endoscopic, laparoscopic, and open surgical procedures, various design features of surgical instruments have been developed to assist surgeon's motions. These design features include, for example, rotatable shafts and articulating wrist mechanisms (e.g., at the end of an instrument). In traditional endoscopic, laparoscopic, and open surgical procedures, the reach to the surgical site is determined by the instrument shaft length and mainly controlled by the surgical user's translational motion. Various shaft lengths have been used to achieve this purpose. In certain situations, it is desirable to have the capability to adjust the shaft length so that the surgeon has flexibility to reach a targeted site and tissue with less translational motion and tool exchange. This in turn will reduce user fatigue, provide higher precision for surgical motions and save procedure time.

The above concerns are particularly applicable to ultrasonic surgical instruments. Ultrasonic surgical instruments have been used for quite some time in the cutting, coagulation and/or dissection of tissue during various medical procedures. Compared to conventional static scalpels, for example, ultrasonically driven blades typically require less force for cutting tissue, and can also provide coagulation of blood vessels—particularly when the instrument includes a clamp arm associated with the blade (commonly referred to as ultrasonic shears). Energy in the form of mechanical vibrations at ultrasonic frequencies is transmitted to a surgical end-effector. Ultrasonic surgical instruments are particularly advantageous because of the amount of ultrasonic energy that may be transmitted from an ultrasonic transducer to the surgical end-effector via a waveguide. Such instruments are particularly suited for use in minimally invasive surgery, such as endoscopic or laparoscopic procedures, wherein the end-effector is typically passed through a trocar or other small opening to reach the surgical site.

Ultrasonic surgical end-effectors, also referred to as blades, are usually provided at the end of an elongate waveguide, which in turn is operatively coupled to an ultrasonic transducer. The transducer is adapted to convert electrical energy (typically supplied by an external generator) into vibrational motion, typically longitudinal vibrations, at an ultrasonic frequency. In many instances, the transducer includes a "Langevin stack" of piezoelectric disks for this purpose. The standing wave produced by the transducer is transmitted from the transducer to the waveguide, and propagates the length of the waveguide to the blade or other ultrasonic end-effector located at the distal end of the waveguide. As a result, end-effector vibrates at an ultrasonic frequency.

When the ultrasonically vibrating blade is urged against tissue, such as by manipulation of a handpiece and/or by clamping tissue between the vibrating blade and a clamp arm, the mechanical vibratory energy of the blade is transmitted to the tissue, not only cutting the tissue but also generating frictional heat and causing cavitation, coaptation and coagulation of the tissue. Such devices having a blade and associated clamp arm for urging tissue against the ultrasonically vibrating blade are referred to as ultrasonic shears (also known as clamp coagulators or ultrasonic forceps). Tissue is urged against the ultrasonic blade (or end-effector) by a movable clamp arm that opposes at least a portion of the blade. During use, tissue positioned between the clamp arm and the blade is compressed against the blade as the clamp arm is closed. As a result, the clamped tissue is cut and coagulated.

While a variety of devices and techniques may exist for providing ultrasonic surgical instruments and ultrasonic waveguides, it is believed that no one prior to the inventors has made or used an invention as described herein.

BRIEF DESCRIPTION OF THE DRAWINGS

While the specification concludes with claims particularly pointing out and distinctly claiming the invention, it is believed that the invention will be better understood from the detailed description of certain embodiments thereof when read in conjunction with the accompanying drawings. Unless the context indicates otherwise, like numerals are used in the drawings to identify similar elements in the drawings. In addition, some of the figures may have been simplified by the omission of certain elements in order to more clearly show other elements. Such omissions are not necessarily indicative of the presence or absence of particular elements in any of the exemplary embodiments, except as may be explicitly stated in the corresponding detailed description.

FIG. 1 depicts a schematic view of one embodiment of an ultrasonic surgical instrument having translational capability such that the effective length can be altered without changing the resonance frequency, wherein the instrument in the configuration of FIG. 1 has a first effective length and the transducer housing is omitted.

FIG. 2 depicts a schematic view of the ultrasonic surgical instrument of FIG. 1, wherein the instrument in the configuration of FIG. 2 has a second effective length shorter than the first effective length in FIG. 1.

Figure 3:
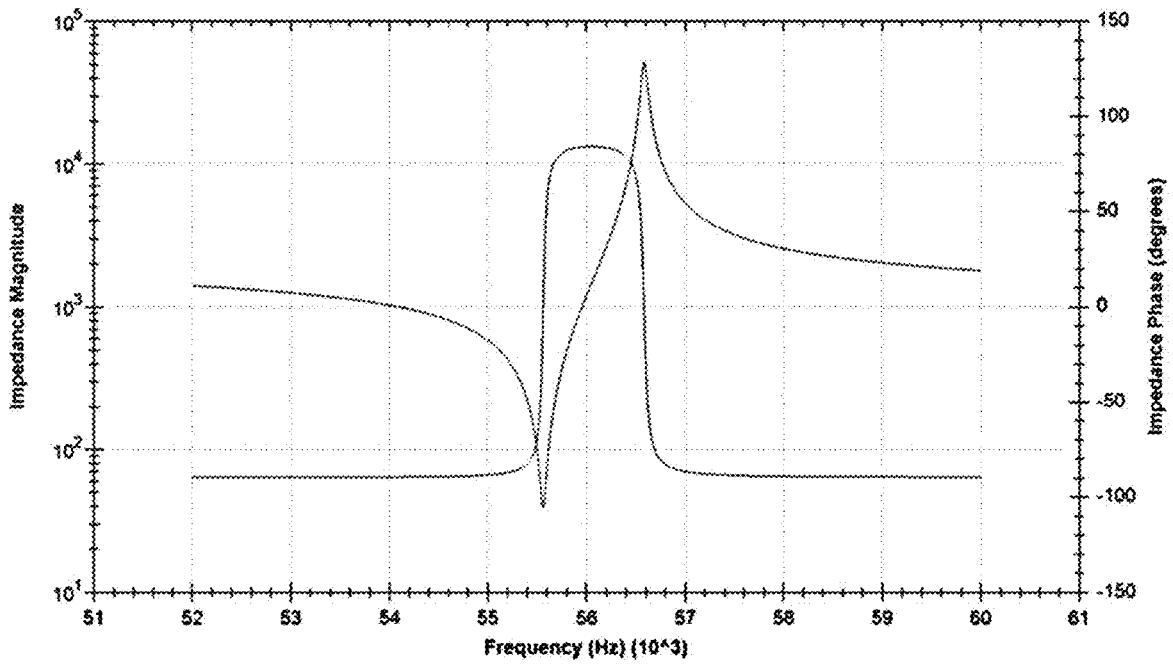
FIG. 3 is an impedance phase diagram of the instrument of FIG. 1.

The drawings are intended to illustrate rather than limit the scope of the present invention. Embodiments of the present invention may be carried out in ways not necessarily depicted in the drawings. Thus, the drawings are intended to merely aid in the explanation of the invention. Thus, the present invention is not limited to the precise arrangements shown in the drawings.

DETAILED DESCRIPTION

The following detailed description describes examples of embodiments of the invention solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention.

Embodiments of the present disclosure provide variable length ultrasonic surgical instruments, wherein the effective length of the instrument can be selectively changed without affecting the resonant frequency of the instrument. In some embodiments, the length can be selectively changed between at least two, at least three, or at least four different effective lengths. As used herein, the "effective length" of the instrument refers to the distance between the location of the distal-most connection between the transducer and the waveguide (which usually is at the distal-most antinode of the transducer, located at the distal end of the transducer) and the distal end of the ultrasonic end effector.

In some embodiments, the end effector (e.g., an ultrasonic blade) is located at the distal end of an elongate waveguide, and a proximal portion of the waveguide is adapted to be operatively coupled to an ultrasonic transducer such that the waveguide will transmit ultrasonic energy from the transducer to the end effector. In some particular embodiments, the proximal portion of the waveguide is adjustably received within an axially extending passageway in the transducer assembly to selectively shorten the effective length of the instrument while still allowing the waveguide to be operatively coupled to the transducer. For example, the waveguide is telescopically received within the interior of the transducer assembly. In some embodiments, the selective adjustment of the effective length of the instrument does not alter the resonance frequency of the instrument.

FIGS. 1 and 2 are schematic illustrations of one embodiment of an ultrasonic surgical instrument (10) comprising an ultrasonic transducer assembly (12) and an elongate waveguide (14) operatively and adjustably coupled to the transducer such that the waveguide extends distally away from the transducer. An end effector in the form of blade (16) is located at the distal end (14B) of the waveguide. The coupling of the waveguide to the transducer is adjustable such that that the instrument (10) can be configured to have two or more effective lengths.

The transducer assembly (12) is operable to drive the ultrasonic end effector (16). In the embodiment shown, the transducer assembly (12) includes a stack (plurality) of piezoelectric disks (20) that convert electrical energy, supplied by an external generator, into longitudinal vibrational motion at an ultrasonic frequency. A standing wave is transmitted from the transducer assembly to the waveguide (14) and propagates the length of the waveguide to the end effector (e.g., a cutting blade) (16). A proximal end mass (24) is located proximal the to the piezoelectric disks (20), and a center bolt (26) is used to secure the transducer assembly components to one another. The transducer assembly (12) further includes a distal portion comprising a horn (22). The positive and negative interleaved electrodes used to drive the piezoelectric disks and an electrical connector (e.g., at the proximal end of the transducer assembly) for operable connection to an ultrasonic generator are not shown in FIGS. 1 and 2. A housing, described below, is typically provided for the transducer assembly.

The proximal end mass and piezoelectric disks are generally annular in shape. The center bolt (26) includes an externally threaded shaft (28) which extends through the central aperture (33) of the proximal end mass and the central apertures (34) of the piezo disks. The threaded distal end of the bolt shaft (28) is threadably received in a threaded bore (35) in the distal end of the horn (22). The center bolt not only secures the piezo disks to the distal end mass and horn, but also preloads the piezo stack. In the embodiment shown, the threaded shaft (28) also includes an internal bore (30) that is axially aligned with an internal bore (32) extending through the horn (22), from the distal end of the spacer to the threaded bore (35). Thus, an axially extending passageway extends though the transducer assembly, from the distal end of the assembly to the proximal head of the center bolt. In the embodiment shown, this passageway terminates at the proximal head of the center bolt. In alternative embodiments, the passageway extends through thickness of the center bolt (i.e., the proximal face of the proximal head of the center bolt has an aperture axially aligned with the passageway through the transducer assembly such that the proximal end portion of the waveguide can extend out the proximal end of the transducer assembly when the waveguide is retracted).

When an electrical signal of appropriate voltage and frequency (e.g., 55.5 kHz) is applied between the electrodes in the transducer assembly, the piezoelectric disks vibrate at an ultrasonic frequency. The piezoelectric disks will resonate, producing a standing vibrational wave that propagates through the length of the horn. The standing wave produced in the transducer exhibits the nodes and antinodes shown in FIG. 2. In this particular embodiment, the transducer assembly (12) has a half-wave design. It will be understood, however, that the present disclosure is not limited to half-wave transducers. Full-wave transducers may also be used, wherein the transducer exhibits an additional node and antinode.

The axially extending internal passageway in the transducer assembly (i.e., provided by internal bore (30) of the bolt shaft (28) and the internal bore (32) of the horn (22)) has an internal diameter that is slightly larger than the outer diameter of the proximal end portion (14A) of the waveguide. This allows the waveguide to be received within this internal passageway such that the effective length of the waveguide can be varied depending on the extent of insertion of the proximal end portion of the waveguide into the transducer assembly (12). The waveguide and transducer assembly are configured such that, in the first length configuration of FIG. 1, the proximal end portion (14A) of the waveguide extends into the passageway of the transducer assembly only a first distance. (In some embodiments, the proximal end portion (14A) of the waveguide will be coupled to the distal end of the transducer assembly with no portion of the waveguide extending into the passageway.) In the second (shorter) length configuration of FIG. 2, the proximal end portion (14A) of the waveguide extends into the passageway of the transducer assembly a second distance greater than the first distance, thus shortening the effective length of the waveguide. It will be understood that the selectable effective lengths of the waveguide generally should be such that the overall frequency of the instrument will remain the same as (or substantially the same as) the resonant frequency of the transducer assembly. By way of example, one or more flat areas can be machined in the waveguide to facilitate insertion of the waveguide into the passageway of the transducer assembly (and securement thereat) a distance that will maintain the overall frequency of the instrument the same as (or substantially the same as) the resonant frequency of the transducer assembly.

In FIG. 1 the waveguide is fully extended out of the internal passageway in the transducer assembly and operatively coupled (secured) at the distal end of the transducer assembly (in this instance, the distal-most antinode of the transducer). The overall acoustic train length is 140 mm, wherein the acoustic train length refers to the distance between the proximal end of the transducer assembly (i.e., the distal-most antinode of the transducer) and the distal tip of the end effector. In FIG. 2, a greater portion of the waveguide is located within the transducer assembly, and operatively coupled (e.g., threadably secured) inside the transducer assembly and, optionally, at the distal end of the transducer assembly. The acoustic train length in FIG. 2 is about 93 mm. However, in both FIG. 1 and FIG. 2, the ultrasonic surgical instrument will resonate at 55.5 kHz.

Figure 4:
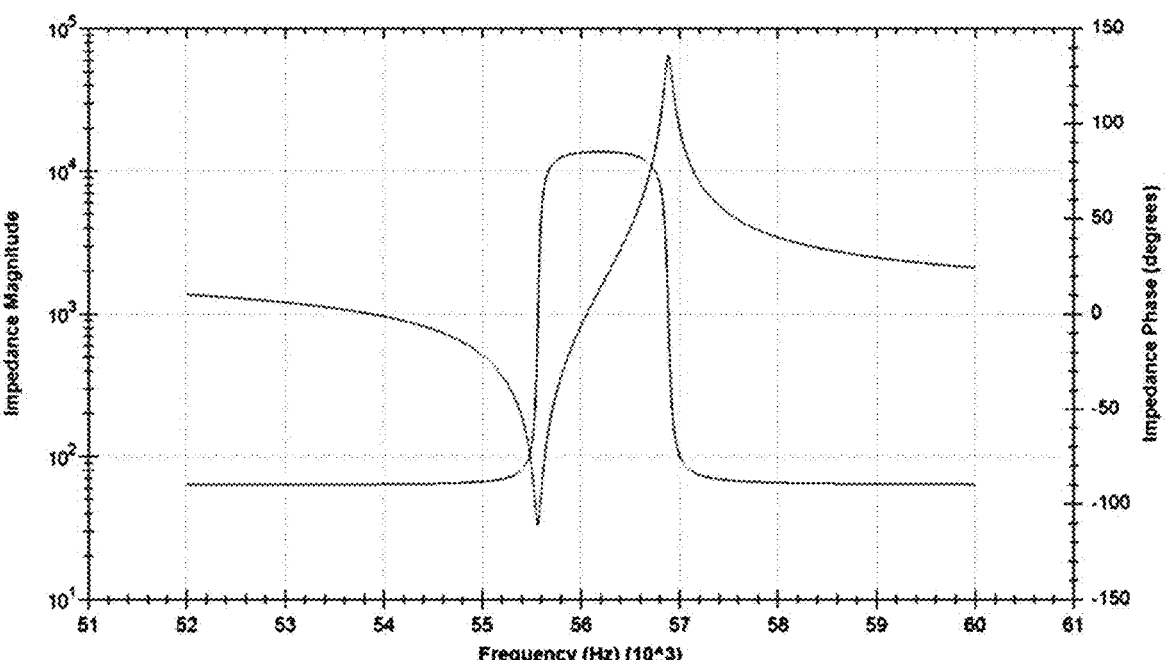
FIG. 4 is an impedance phase diagram of the instrument of FIG. 2.

FIG. 3 depicts an impedance phase diagram for the instrument configuration of FIG. 1, showing the magnitude and phase of impedance as a function of frequency. FIG. 4 depicts an impedance phase diagram for the instrument configuration of FIG. 2, showing the magnitude and phase of impedance as a function of frequency. As seen in FIGS. 3 and 4, the resonant frequency is the same (55.5 kHz) in both configurations.

As noted above, the transducer assembly (12) has a half-wave design. However, a full wave or other multiple of half wave length transducers can be employed, particularly to allow for greater differences in effective lengths and/or more selectable effective lengths (e.g., at least four different lengths) without causing a resonant frequency shift. By providing a transducer assembly having a multiple of half waves (e.g., a full wave, 1.5 waves, or 2 waves), the node locations stay substantially the same, which facilitates mounting the waveguide to supporting mechanical components such as an outer support tube in which the waveguide may be supported (as described below). For example, this allows support rings (e.g., silicone rings) to be positioned at one or more of the nodes for supporting the waveguide within the interior of an outer support tube. The instrument can also be configured for any desired resonant frequency, while still providing variable effective lengths for the instrument.

The waveguide, blade, and transducer can be made from a variety of materials, with a variety of configurations. For example, in the embodiment of FIGS. 1 and 2, the transducer assembly comprises four lead zirconate titanate ("PZT") disks (20), an aluminum horn (22), and a titanium center bolt (26). Also in the embodiment of FIGS. 1-7, the waveguide (14) and blade (16) have a unitary construction comprising a single piece of machined aluminum (or aluminum alloy), fabricated such as by milling a single metal rod so as to provide the depicted features. In alternative embodiments, waveguide (14) comprises two or more portions joined to one another (e.g., by threaded attachment, adhesive, welding, or other suitable ways known to those skilled in the art). Similarly, although blade (16) is depicted as being integral with waveguide (14), in alternative embodiments the blade (16) is a separate structure that is attached to the distal end of the waveguide, such as by threaded attachment, adhesive, or welding.

The waveguide (14) can also include internal or external threads on its proximal end portion (14A), and optionally at a location distal thereto, to facilitate operative coupling to the transducer (e.g., to the horn (22), and/or the shaft (28) of the center bolt (26). By way of example, at least the proximal end portion (14A) can be externally threaded for mating engagement with internal threads within at least distal portion (22A) of the internal bore (32) of the horn (22) and internal threads within at least a portion of the internal bore (30) of the shaft (28) of the center bolt (26). The external threads on the proximal end portion (14A) of the waveguide can have slightly larger diameter than the portion of the waveguide distal thereto, thereby allowing the waveguide to telescope inwardly into the transducer once the threaded proximal end portion (14A) proximally clears the threaded distal portion (22A) of the internal bore (32) of the horn (22). Thus, the externally threaded proximal end portion (14A) of the waveguide can be threadably secured within a distal threaded portion of the internal bore (32) of the horn (22), as seen in FIG. 1. When the waveguide is retracted (telescoped proximally) within the transducer assembly, the externally threaded proximal end portion (14A) of the waveguide can be threadably secured within a proximal threaded portion of the internal bore (30) of the shaft (28) of the center bolt (26), as seen in FIG. 2. In an alternative embodiment, a second portion of the waveguide distal to the proximal end portion (14A) is externally threaded such that, when configured as shown in FIG. 2, the second externally threaded portion of the waveguide is threadably secured within the distal threaded portion of the internal bore (32) of the horn (22) (i.e., immediately proximal to the distal-most antinode of the transducer).

The ultrasonic surgical instrument comprising transducer assembly (12), waveguide (14) and end effector (16) shown in FIGS. 1 and 2 may be used as depicted, with the transducer assembly including an outer housing (84) (see FIG. 7) in which the piezoelectric disks (20), horn (20), proximal end mass (24), and center bolt (26) are located. Housing (84) is configured to facilitate grasping and manipulation of the transducer housing (84) by a medical practitioner. The proximal end of the housing includes an electrical connector (e.g., a plug or a socket) for operative connection to an ultrasonic generator (80) via a mating connector (81) provided at the end of a cable operatively connected to the generator (80). Thus, an electrical drive signal comprising an alternating current of ultrasonic frequency is supplied from the generator (80) to the transducer (12) via the cable and connector (81). Transducer (12) converts the drive signal into a standing, ultrasonic vibrational wave in the transducer, including the distal portion (22A) of the transducer horn (22) which is accessible from the distal end of housing (84). In some instances, the transducer housing (84) also includes a threaded projection (89) at its distal end, adjacent distal portion (22A) of the transducer horn, for attachment of a sheath (or support tube) assembly described below.

Figures 5, 6:
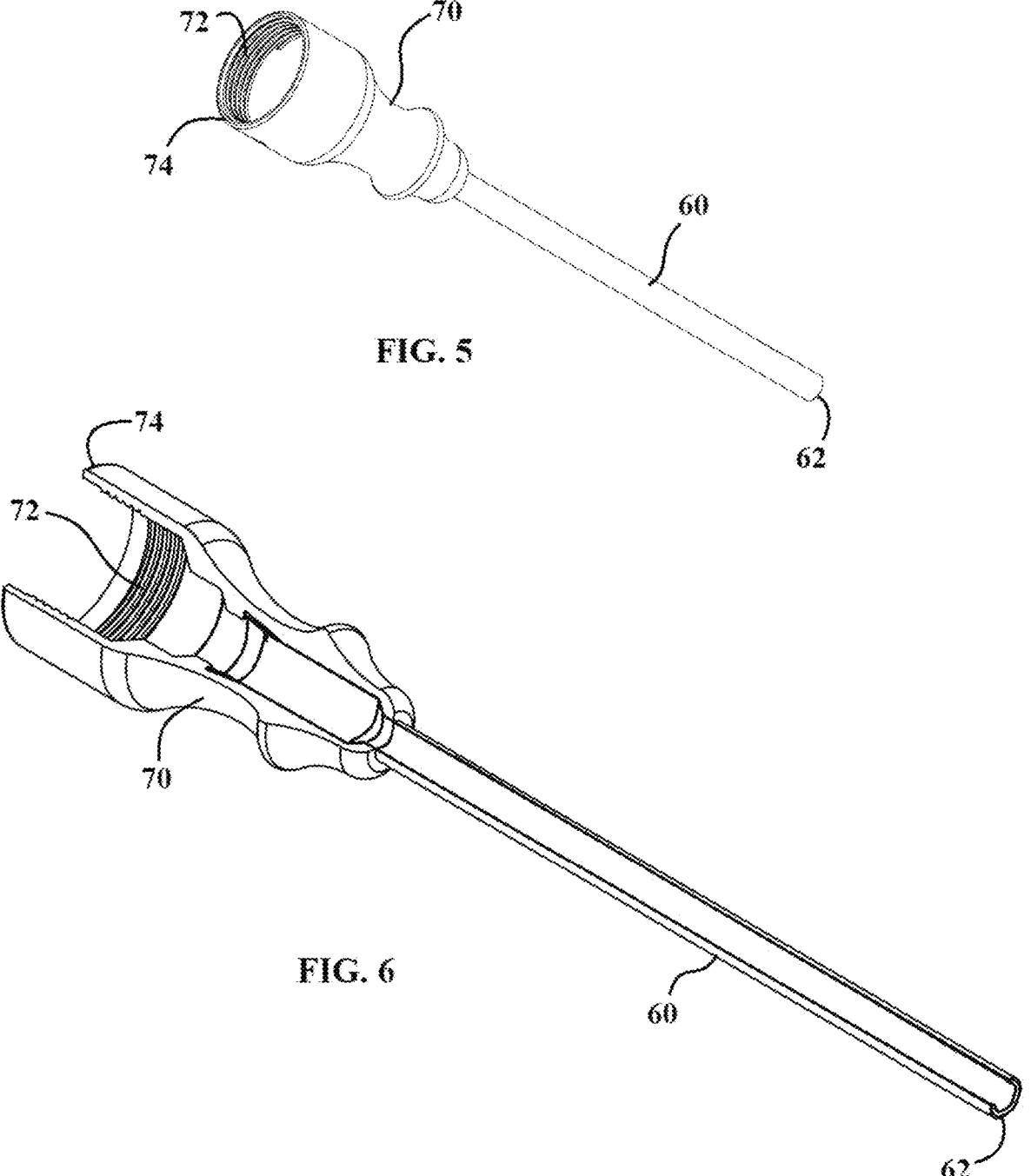
FIG. 5 depicts a perspective view of one embodiment of a support tube assembly for use with the ultrasonic surgical instrument of FIG. 1.
FIG. 6 depicts a partially cross-sectional view of the support tube assembly of FIG. 5.
Figure 7:
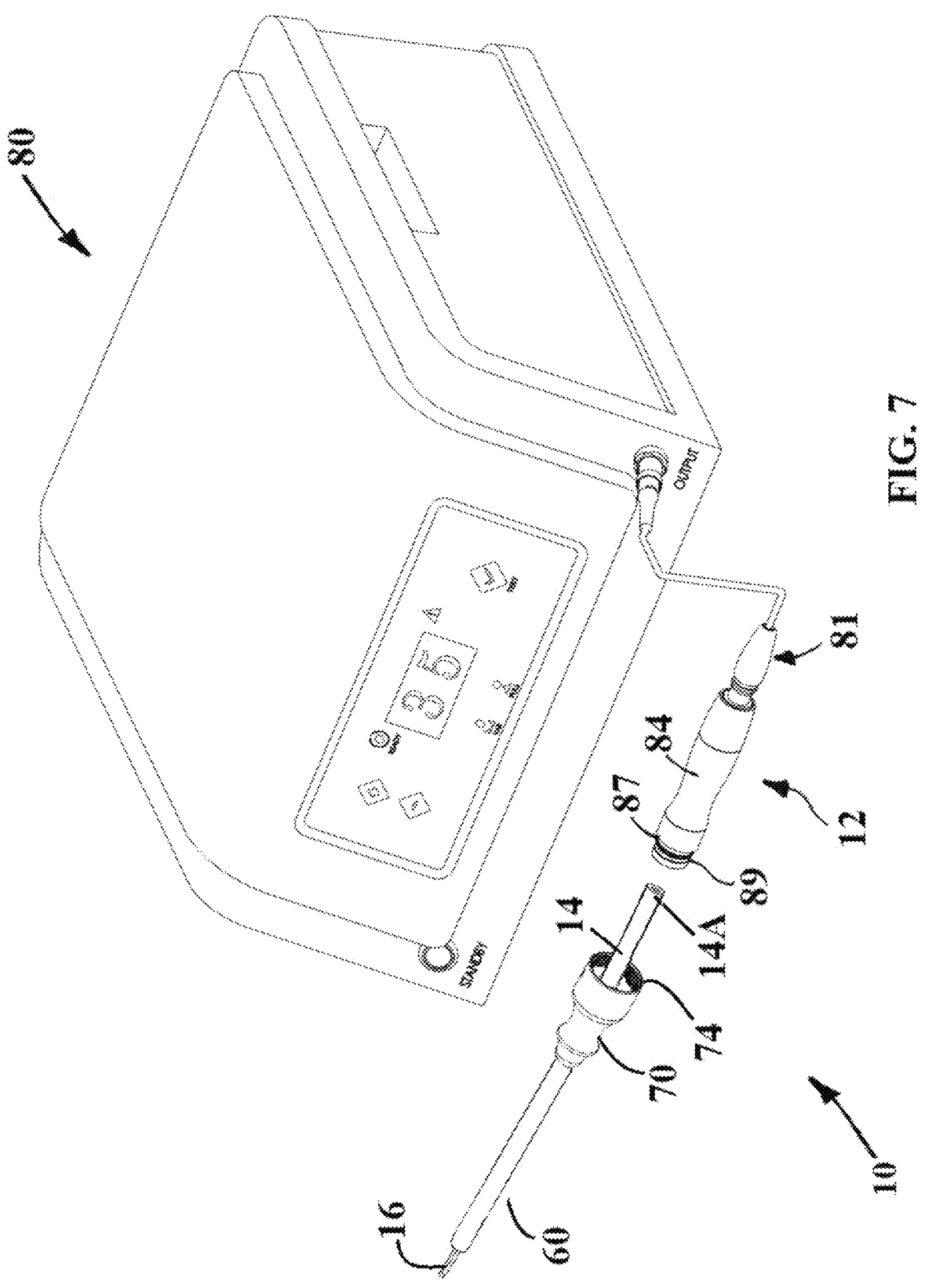
FIG. 7 depicts a the ultrasonic surgical instrument of claim 2 operatively connected to an ultrasonic generator, the instrument shown with the waveguide and support tube assembly detached from the transducer assembly.

While the ultrasonic surgical instrument (10) can be used without an outer support tube, in some embodiments the ultrasonic surgical instrument further includes a support tube (also referred to as a sheath) in which the waveguide is supported, with at least a portion of the blade (and optionally a portion of the waveguide) extending away from a distal end of the support tube. FIGS. 5-7 depict an exemplary support tube assembly comprising a hollow cylindrical support tube (60) and a support tube coupler (70) at the proximal end of the support tube (60).

Support tube (60) not only protects the waveguide (14), but also prevents inadvertent contact between the waveguide (14) and the patient, medical personnel or the surgical environment. Not only will such contact damp vibration of the waveguide (14), but it can also cause injury to the patient or medical personnel since the waveguide (14) is ultrasonically vibrating. In the embodiment shown in FIG. 7, the waveguide (14) is located within the support tube (60) and support tube coupler (70), with a proximal portion of the waveguide extending proximally away from the proximal end of the coupler (70) for receipt within the transducer. However, the support tube assembly is not secured directly to the waveguide (14). Instead, waveguide (14) is operatively coupleable at its proximal end to the transducer (22), and support tube coupler (70) is secured to the transducer housing (84).

The waveguide (14) includes an internally threaded connector portion (14) at its proximal end, as well as a plurality of flats (16) arrayed about the circumference of the waveguide (14) adjacent to connector portion (14). The flats (16) provide an integral nut on waveguide (14) for use in tightening the waveguide onto a transducer, as explained below. While waveguide (14) is depicted as being of unitary construction, in alternative embodiments waveguide (14) comprises two or more portions joined to one another (e.g., by threaded attachment). For example, in one alternative embodiment, connector portion (14) and flats (16) comprise a unitary structure which is threadably attached at the proximal end of waveguide (14) (e.g., by use of an internally threaded bore and a mating threaded stud connecting the two portions of the waveguide (14)). Similarly, although blade (24) is depicted as being integral with waveguide (14), in alternative embodiments the blade (24) is a separate structure that is attached to the distal end of waveguide (14), such as by threaded attachment.

It will be understood that FIG. 7 depicts the support tube assembly for use when the waveguide (14) is coupled to the transducer (12) in the retracted configuration shown in FIG. 2. When the waveguide is coupled to the transducer (12) in the extended configuration shown in FIG. 1, a support tube assembly having a longer support tube (60) is used. Thus, some embodiments of the present disclosure comprise an ultrasonic surgical instrument comprising a transducer assembly, a waveguide having an end effector at a distal wherein a proximal portion of the waveguide is selectively coupleable within the transducer assembly to provide at least two different effective lengths, and two or more support tube assemblies having support tubes of different lengths.

As further described in U.S. Pat. No. 11,058,449 ("the '449 patent"), incorporated by reference herein, the waveguide (14) and support tube (60) can include a variety of other features for facilitating the ultrasonic vibration of the waveguide and end effector, including minimizing dampening and/or enhancing rigidity. For example, during use of the ultrasonic surgical devices described herein, various forces applied at the end effector (16) will tend to cause lateral deflection of the waveguide (14) within the support tube (60). In order to prevent contact between the inner wall of support tube (60) and blade (24) and waveguide (14), thereby limiting or preventing potential damage to the ultrasonic device (10) as well as damping of the standing wave, one or more spacers can be provided between the waveguide (14) and the interior of support tube (60) in order to maintain the waveguide (14) in the center of the support tube (60) (i.e., the longitudinal axis of the waveguide (14) aligned with the longitudinal axis of the support tube (60)). For example, and as shown in the '449 patent, one or more resilient rings can be provided on the exterior of waveguide (14). These rings can comprise, for example, silicone rings. Since the amplitude of the longitudinal vibration of the waveguide (14) at the driving frequency (e.g., 55.5 kHz) during use is zero at the nodes of the standing wave, the resilient rings can be located at or near the vibrational nodes of the waveguide (14) in order to limit damping of the standing wave. These rings will also dampen any vibrations having frequencies other than the drive frequency, since the nodes of vibrations of other frequencies will generally not coincide with the node locations for the drive frequency.

As further described in the '449 patent, the resilient rings can be supported and maintained in place in a variety of ways known to those skilled in the art. For example, an annular support can be provided on the waveguide for each resilient ring, and the resilient ring then insert molded over the support or secured over the annular support in other ways known to those skilled in the art (e.g., adhesively, bonding, etc.). Annular supports can be formed, for example, by lathe turning. As yet another alternative, a circumferential groove can be provided on the waveguide (e.g., by lathe turning so as to form two adjacent rings with the groove located therebetween). The resilient ring can then be maintained in position mechanically by trapping the ring within the groove. Similar arrangements may be employed for securing additional resilient rings about the waveguide. In some embodiments, resilient rings are provided at or near two or more vibrational nodes, depending in part on the length of the waveguide.

As is known to those skilled in the art, a variety of other features may be provided on the waveguide (14). For example, and as described in the '449 patent, the waveguide (14) can include a plurality of segments of varying diameter, with tapers providing a smooth transition between segments of different diameters. Changes in diameter of the waveguide along its length serve to, among other things, adjust the amplitude and/or frequency of the vibrational wave propagating the length of the waveguide (14).

As mentioned previously, the support tube assembly comprises a cylindrical support tube (or sheath) (60) and a support tube (or sheath) coupler (70), which are affixed to one another as shown. The support tube (60) may be affixed to the support tube coupler (70) in a variety of ways such as by welding, adhesive and/or swaging.

Support tube coupler (70) is generally hollow and includes a threaded cavity (72) extending inwardly away from proximal end wall (74) of the coupler (70). Once the waveguide (14) has been operatively coupled to the transducer (22) to provide the desired effective length in the manner described previously, the support tube assembly is slid over the waveguide (14). In particular, end effector (16) is inserted through the threaded cavity (72) followed by waveguide (14). Thereafter, support tube coupler (70) is threadably secured to the transducer housing (84) by the threaded engagement of threaded projection (89) within threaded cavity (72), with the proximal end wall (74) of the coupler (70) in abutment with the end wall (87) of transducer housing (84). Once assembled in this manner, at least a portion of the end effector (16) extends beyond the distal end wall (62) of support tube (60), as seen in FIG. 7. In other words, in some embodiments, a proximal portion of the end effector is positioned within the support tube, while a distal portion of the blade extends beyond the distal end wall of the support tube (as depicted in FIG. 7). Of course, it will be understood that the waveguide (14), end effector (16), and/or support tube assembly can be configured such that either more or less of the end effector (16) extends beyond the distal end (62) of support tube (60). In general, enough of end effector (16) should protrude beyond the distal end of support tube (60) to provide adequate visualization, reach, and manipulation of the end effector for cutting, dissection and/or coagulation during use, while not having so much of the end effector (16) exposed that there is a heightened risk of unintended contact between the end effector and tissue.

The blade (16) may have any of a variety of shapes and configurations, such as being straight or curved, and having any of a variety of features such as multiple cutting edges and/or one or more hook portions. In some instances, a clamp member is operatively located adjacent to the blade for selective engagement with a face and/or an edge of the blade so as to provide for both coagulating and cutting, thus providing an ultrasonic shears instrument. With or without an associated clamp member, the blade (16) may be used for ultrasonically cutting, coagulating and/or dissecting tissue.

Figure 8:
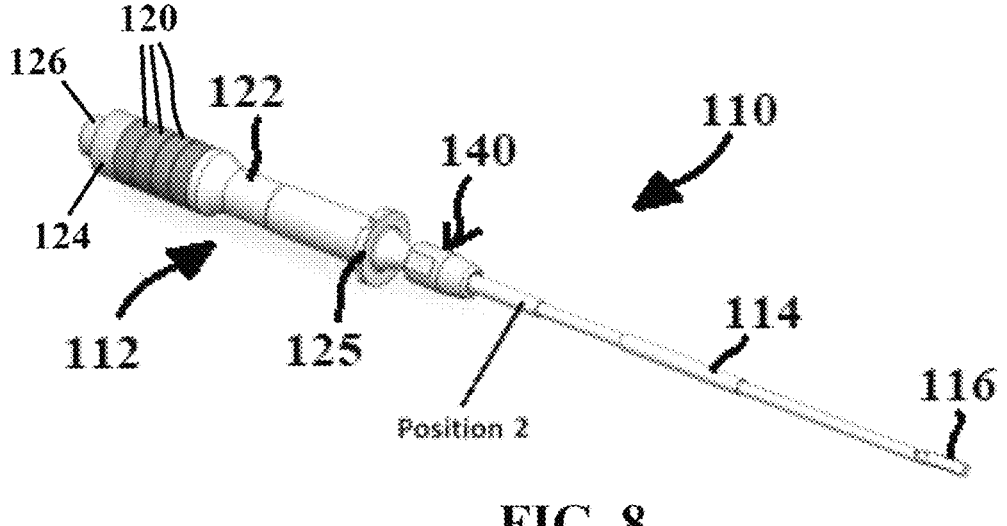
FIG. 8 depicts a schematic view of another embodiment of an ultrasonic surgical instrument having translational capability such that the effective length can be altered without changing the resonance frequency, wherein the instrument in the configuration of FIG. 1 has a first effective length and the transducer housing is omitted.
Figure 9:
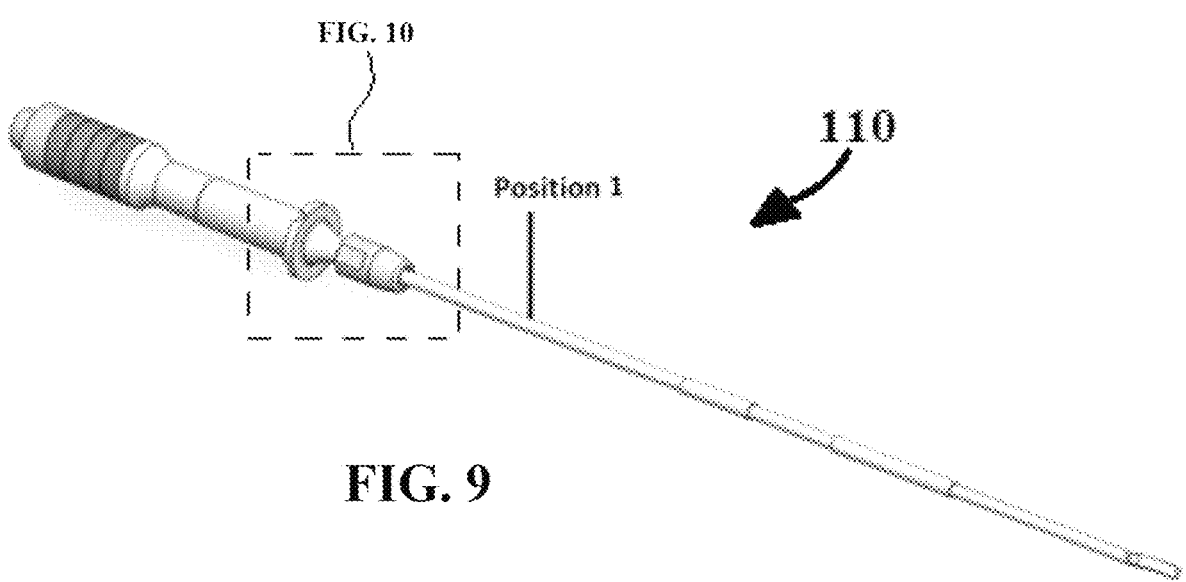
FIG. 9 depicts a schematic view of the ultrasonic surgical instrument of FIG. 8, wherein the instrument in the configuration of FIG. 9 has a second effective length longer than the first effective length in FIG. 8.
Figure 10:
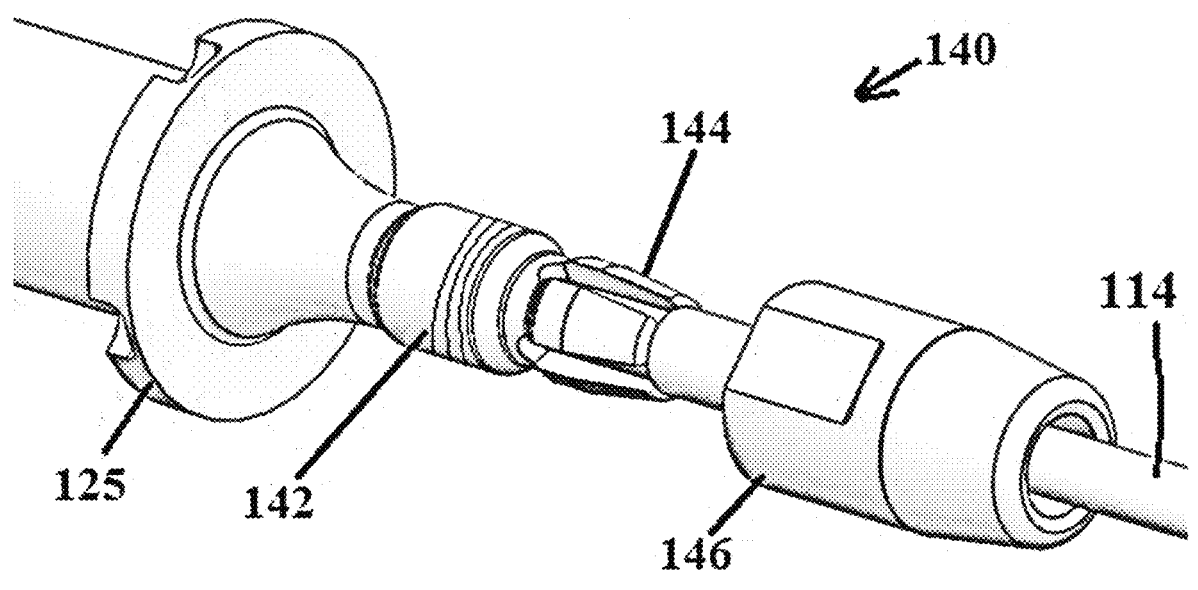
FIG. 10 depicts an enlarged view of a portion of the instrument of FIG. 9.

FIGS. 8-11 depict an alternative embodiment of an ultrasonic surgical instrument (110) according to the present disclosure, comprising an ultrasonic transducer assembly (112) having a full wave design, an elongate waveguide (114) operatively coupleable to the transducer, an end effector in the form of blade (116) at the distal end of the waveguide, and an adjustable coupling assembly (140) for selectively coupling the waveguide to the transducer assembly such that the effective length of the instrument can be varied without altering the resonant frequency of the instrument (e.g., ±0.5 kHz, ±0.2 kHz, or ±0.1 kHz). In FIG. 8, the waveguide is at a second position such that the effective length is shorter as compared to when the waveguide is at a first position shown in FIG. 9.

It will be understood that the transducer housing (e.g., similar to housing (84) is omitted in FIGS. 8-11. The transducer assembly (112) is similar to transducer assembly (22) in FIGS. 1 and 2. Also, a support tube assembly (e.g., similar to that described previously) can be used with the embodiment of FIGS. 8-11, with the support tube mounted to the transducer housing (e.g., in the manner described previously) after the effective length has been adjusted to the desired length.

Once again the transducer assembly (112) includes a stack of piezoelectric disks (120), and a distal portion comprising a horn (122). A proximal end mass (124) is located proximal the to the piezoelectric disks and a center bolt (126) is used to secure the transducer assembly components to one another. In this instance, a mounting flange (125) is also provided on a distal portion of the transducer assembly, and can be used to flexibly support the transducer within the housing. As before, an internal passageway extends axially through the interior of the transducer assembly, as seen in the cross-sectional view of FIG. 11, wherein a bore (132) extends axially through a distal portion of the transducer assembly. The bore is sized to adjustably receive the waveguide (114) therein for adjusting the effective length of the instrument. The effective length is shortened, for example, by advancing the proximal end portion of the waveguide further into the transducer assembly, in the proximal direction.

In the embodiment of FIGS. 8-11, an adjustable coupling assembly (140) is used to adjustably and operatively couple the waveguide to the transducer assembly. The coupling assembly (140) includes an externally threaded neck (142) and distal collet (144) on the distal end portion of the transducer assembly. The threaded neck is located distal to the mounting flange (125), and the collet (144) is located distal to the threaded neck. In some embodiments, the externally threaded neck (142) and distal collet (144) are integral with the mounting flange (125), and at least the distal portion of the horn (122) immediately adjacent the mounting flange (or even the entirety of the horn (122)). The bore (132) extends through the neck (142) and collet (144), proximally past the mounting flange (125) and through at least a portion of the horn (122) (or even the entire length of the horn). The bore (132) is configured for adjustably receiving a proximal portion of the waveguide (114) therein. The effective length of the instrument is selectively adjusted by the depth that the waveguide is inserted into the bore (132). In some embodiments, the waveguide (114) can be received within an internal bore of the bolt shaft of the center bolt (126), similar to the previously described embodiment, when the waveguide is moved to its fully retracted position.

Figure 11:
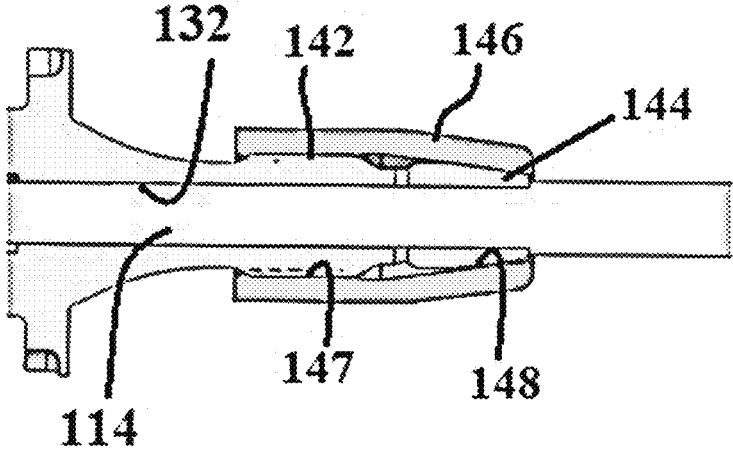
FIG. 11 depicts a cross-sectional view of the portion of the instrument shown in FIG. 10.

The coupling assembly (140) further includes a locking member in the form of locking nut (146), configured to receive a portion of the waveguide therethrough. The locking nut includes an internally threaded proximal portion (147), and a tapered distal portion (148). To variably and operatively couple the waveguide (114) to the transducer assembly, the proximal end of the waveguide is inserted through the locking nut (146) and into the bore (132) of the transducer assembly through the distal end thereof. Once the waveguide is at the desired depth, the locking nut (146) is slide over the collet (144) and threaded onto the neck (142). As the locking nut is threaded further along the neck, the tapered distal portion (148) of the locking nut clamps (or compresses) the collet (144) against the waveguide, thereby operatively and securely coupling the waveguide to the transducer assembly. Visible indicia may be provided on the waveguide for ensuring that the waveguide is inserted into the transducer assembly at one or two or more depths that ensure that the waveguide and blade will vibrate at the desired resonant frequency (i.e., to ensure that one of the resonant effective lengths is met). Alternatively, circumferential shoulders can be provided on the waveguide such that the distal end of the collet (144) abuts against the shoulder (e.g., as seen in FIG. 11).

While various embodiments of variable length ultrasonic surgical instruments have been described in detail above, it will be understood that the components, features and configurations, as well as the methods of manufacturing the devices and methods described herein are not limited to the specific embodiments described herein.

What is claimed is:

1. An ultrasonic surgical instrument having an ultrasonic resonant frequency when operatively connected to an ultrasonic generator, the surgical instrument comprising:

(a) an ultrasonic transducer assembly adapted for converting electrical energy into longitudinal vibrational motion at an ultrasonic frequency, the transducer assembly having an axial passageway extending proximally from a distal end of the transducer through at least a portion of a length of the transducer assembly;

(b) an ultrasonic waveguide having a proximal portion and a distal end;

(c) an end effector at the distal end of the waveguide; and (d) first and second support tube assemblies, each of said support tube assemblies comprising a hollow support tube with the support of the first support tube assembly longer than the support tube of the second support tube assembly;

wherein the proximal portion of the waveguide is adapted to be operatively and selectively coupled within the axial passageway of the ultrasonic transducer such that the waveguide will transmit ultrasonic energy from the transducer to the end effector, and further wherein the waveguide is selectively coupleable within the transducer to provide at least two different effective lengths without altering the resonant frequency of the instrument; and further wherein said first and second support tube assemblies are selectively mountable to the transducer assembly with the waveguide positioned within the support tube of the support tube assembly.

2. The ultrasonic surgical instrument of claim 1, wherein the proximal portion of the waveguide is telescopically received within the axial passageway of the transducer assembly.

3. The ultrasonic surgical instrument of claim 2, wherein the transducer assembly comprises a horn and a plurality of piezoelectric disks proximal to the horn that convert the electrical energy into the longitudinal vibrational motions in the horn.

4. The ultrasonic surgical instrument of claim 3, wherein the transducer assembly further comprises a center bolt for securing the piezoelectric disks and horn to one another, wherein the axial passageway extends into at least a portion of the center bolt.

5. The ultrasonic surgical instrument of claim 4, wherein the center bolt includes a bolt shaft, and wherein said axial passageway extends through the length of the horn and into at least a portion of the bolt shaft of the center bolt.

6. The ultrasonic surgical instrument of claim 5, wherein the transducer assembly further comprises an end mass and the center bolt comprises a proximal head at a proximal end of the bolt shaft, wherein the end mass is located between the proximal head of the center bolt and the piezoelectric disks, and further wherein the axial passageway extends through the end mass.

7. The ultrasonic surgical instrument of claim 3, wherein the transducer assembly further comprises a housing in which the piezoelectric disks and at least a portion of the horn are located.

8. The ultrasonic surgical instrument of claim 7, wherein each support tube assembly further comprises a support tube coupler at a proximal end of the support tube, each of said support tube couplers mountable to said housing.

9. The ultrasonic surgical instrument of claim 2, wherein the transducer assembly is a half-wave transducer.

10. The ultrasonic surgical instrument of claim 1, wherein the resonant frequency of the ultrasonic surgical instrument at said at least two effective wavelengths is 55.5 kHz.

11. An ultrasonic surgical instrument having an ultrasonic resonant frequency when operatively connected to an ultrasonic generator, the surgical instrument comprising:

(a) an ultrasonic transducer assembly adapted for converting electrical energy into longitudinal vibrational motion at an ultrasonic frequency, the transducer assembly having an axial passageway extending proximally from a distal end of the transducer through at least a portion of a length of the transducer assembly;

(b) an ultrasonic waveguide having a proximal portion and a distal end; and (c) an end effector at the distal end of the waveguide;

wherein the proximal portion of the waveguide is adapted to be operatively and selectively coupled within the axial passageway of the ultrasonic transducer such that the waveguide will transmit ultrasonic energy from the transducer to the end effector, and further wherein the waveguide is selectively coupleable within the transducer to provide at least two different effective lengths without altering the resonant frequency of the instrument;

further comprising a coupling assembly for selectively coupling the waveguide to the transducer assembly, wherein the coupling assembly comprises a collet located distal to the horn, and a locking member, wherein the collet, and locking member are axially aligned and are configured to receive the proximal portion of the waveguide therethrough such that the locking member slides along the exterior of the waveguide and is secureable over the collet for selectively coupling the waveguide to the transducer assembly.

12. The ultrasonic surgical instrument of claim 11, wherein the locking member comprises a locking nut.

13. The ultrasonic surgical instrument of claim 12, wherein the coupling assembly further comprises an externally threaded neck proximal to said collet, wherein the threaded nut is threadably securable to said neck and over said collet such that the threaded nut compresses the collet against the waveguide.

14. The ultrasonic surgical instrument of claim 12, wherein a proximal portion of the locking nut is internally threaded, and a distal portion of the locking nut is tapered.

15. The ultrasonic surgical instrument of claim 11, wherein the transducer assembly comprises a horn and a plurality of piezoelectric disks proximal to the horn that convert the electrical energy into the longitudinal vibrational motions in the horn.

16. The ultrasonic surgical instrument of claim 15, wherein the transducer assembly further comprises a housing in which the piezoelectric disks and at least a portion of the horn are located.

17. The ultrasonic surgical instrument of claim 11, wherein the transducer assembly is a half-wave transducer, and the resonant frequency of the ultrasonic surgical instrument at said at least two effective wavelengths is 55.5kHz . . .

18. An ultrasonic surgical instrument having an ultrasonic resonant frequency when operatively connected to an ultrasonic generator, the surgical instrument comprising:

(a) an ultrasonic transducer assembly adapted for converting electrical energy into longitudinal vibrational motion at an ultrasonic frequency, the transducer assembly having an axial passageway extending proximally from a distal end of the transducer through at least a portion of a length of the transducer assembly;

(b) an ultrasonic waveguide having a proximal portion and a distal end; and (c) an end effector at the distal end of the waveguide;

wherein the proximal portion of the waveguide is adapted to be operatively and selectively coupled within the axial passageway of the ultrasonic transducer such that the waveguide will transmit ultrasonic energy from the transducer to the end effector, and further wherein the waveguide is selectively coupleable within the transducer to provide at least two different effective lengths without altering the resonant frequency of the instrument;

wherein at least a portion of the axial passageway of the transducer assembly is threaded, a proximal end portion of the waveguide is threaded and is selectively threadably coupleable within the threaded axial passageway of the transducer assembly; and further wherein the threaded proximal end portion of the waveguide has a larger diameter than a portion of the waveguide immediately distal to the threaded proximal end portion.

19. The ultrasonic surgical instrument of claim 18, wherein the transducer assembly comprises a horn and a plurality of piezoelectric disks proximal to the horn that convert the electrical energy into the longitudinal vibrational motions in the horn.

20. The ultrasonic surgical instrument of claim 18, wherein the transducer assembly is a half-wave transducer, and the resonant frequency of the ultrasonic surgical instrument at said at least two effective wavelengths is 55.5 kHz.

* * * * *